United States Patent
Skov et al.

(10) Patent No.: US 9,526,714 B2
(45) Date of Patent: Dec. 27, 2016

(54) METHOD FOR TREATING SKIN LESIONS WITH INGENOL MEBUTATE

(71) Applicant: LEO Laboratories Limited, Dublin (IE)

(72) Inventors: Torsten Skov, Ballerup (DK); Anita Melgaard, Ballerup (DK)

(73) Assignee: LEO Laboratories Limited, Dublin (IE)

( * ) Notice: Subject to any disclaimer, the term of this patent is extended or adjusted under 35 U.S.C. 154(b) by 172 days.

(21) Appl. No.: 14/224,063

(22) Filed: Mar. 24, 2014

(65) Prior Publication Data

US 2015/0265567 A1    Sep. 24, 2015

(51) Int. Cl.
| | |
|---|---|
| *A61K 31/21* | (2006.01) |
| *A01N 37/00* | (2006.01) |
| *A61K 31/22* | (2006.01) |
| *A61K 31/00* | (2006.01) |

(52) U.S. Cl.
CPC ............... *A61K 31/22* (2013.01); *A61K 31/00* (2013.01)

(58) Field of Classification Search
CPC ....................................................... A61K 31/22
USPC ................................................ 514/510, 511
See application file for complete search history.

(56) References Cited

U.S. PATENT DOCUMENTS

| | | | | |
|---|---|---|---|---|
| 7,449,492 | B2 | 11/2008 | Aylward et al. | |
| 8,377,919 | B2 * | 2/2013 | Brown ................. | A61K 9/0014 514/183 |
| 8,653,133 | B2 * | 2/2014 | Ogbourne ............. | C07C 67/52 514/511 |
| 8,735,375 | B2 * | 5/2014 | Brown ................. | A61K 9/0014 514/83 |
| 2013/0251782 | A1 * | 9/2013 | Ladefoged .......... | A61K 9/0014 424/445 |
| 2014/0242012 | A1 * | 8/2014 | Cozzi .................... | A61K 31/22 424/62 |
| 2014/0249218 | A1 * | 9/2014 | Ogbourne ............. | A61K 31/22 514/511 |
| 2015/0119433 | A1 * | 4/2015 | Selmer ................. | A61K 9/0014 514/378 |
| 2015/0119434 | A1 * | 4/2015 | Selmer ................. | A61K 9/0014 514/378 |
| 2015/0258071 | A1 * | 9/2015 | Selmer ................. | A61K 9/0014 514/378 |
| 2016/0089362 | A1 * | 3/2016 | Selmer ................. | A61K 9/0014 514/378 |

FOREIGN PATENT DOCUMENTS

| | | |
|---|---|---|
| WO | WO-2007/068963 A2 | 6/2007 |
| WO | WO-2010/091472 | 8/2010 |
| WO | WO-2011/128780 | 10/2011 |
| WO | WO-2012/176015 | 12/2012 |

OTHER PUBLICATIONS

Lebwohl et al., "Long-term Follow-up Study of Ingenol Mebutate Gel for the Treatment of Actinic Keratoses", Jun. 2013, JAMA Dermatology, vol. 149, No. 6, pp. 666-670.*

Miriam S. Bettencourt MD, "Use of Ingenol Mebutate Gel for Actinic Keratosis in Patients in a Community Dermatology Practice", Mar. 1, 2014, Journal of Drugs in Dermatology, vol. 13, Issue 3, pp. 269-273.*

G. Martin et al., "Clinical findings using ingenol mebutate gel to treat actinic keratoses", J Am Acad Dermatol, pp. S39-S48 (Jan. 2013).

G. Schmieder, Abstract P2915, American Academy of Dermatology, Poster Abstracts, 68th Annual Meeting, Supplement to the Journal of the American Academy of Dermatology, vol. 62, No. 3 (2010).

B. Berman, "New developments in the treatment of actinic keratosis: focus on ingenol mebutate gel", Clinical, Cosmetic and Investigational Dermatology, vol. 5, pp. 111-122 (2012).

Sayed et al., "Constituents of Egyptian Euphorbiaceae, IX. Irritant and cytotoxic ingenane esters from *Euphorbia paralias* L.", Experientia 36:1206-1207 (1980).

Hohmann et al., "Diterpenoids from *Euphorbia peplus*", Planta Med. 66:291-294 (2000).

Lebwohl et al., "Ingenol Mebutate Gel for Actinic Keratosis", The New England Journal of Medicine, 366:1010-1019 (2012).

Siller et al., "PEP005 (ingenol mebutate) gel, a novel agent for the treatment of actinic keratosis: Results of a randomized, double-blind, vehicle-controlled, multicentre, phase IIa study", *Australasian Journal of Dermatology*, 50, 16-22 (2009).

Anderson et al., "Randomized, double-blind, double-dummy, vehicle-controlled study of ingenol mebutate gel 0.025% and 0.05% for actinic keratosis", J Am Acad Dermatol, vol. 60, No. 6, pp. 934-943 (2009).

Siller et al., "PEP005 (ingenol mebutate) gel for the topical treatment of superficial basal cell carcinoma: Results of a randomized phase IIa trial", *Australasian Journal of Dermatology*, 51, 99-105 (2010).

Ogbourne et al., "Antitumor Activity of 3-Ingenyl Angelate: Plasma Membrane and Mitochondrial Disruption and Necrotic Cell Death", *Cancer Res* 64:2833-2839 (2004).

Ramsay et al., "The sap from *Euphorbia peplus* is effective against human nonmelanoma skin cancers", British Journal of Dermatology, 164, pp. 633-636 (2011).

Li et al., "The Skin Cancer Chemotherapeutic Agent Ingenol-3-Angelate (PEP005) Is a Substrate for the Epidermal Multidrug Transporter (ABCB1) and Targets Tumor Vasculature", *Cancer Res*, 70(11):4509-4519 (2010).

(Continued)

*Primary Examiner* — My-Chau T Tran
(74) *Attorney, Agent, or Firm* — Fish & Richardson P.C.

(57) ABSTRACT

The invention provides novel methods for topical treatment of skin lesions such as actinic keratosis over treatment areas up to 250 cm$^2$.

11 Claims, No Drawings

(56) References Cited

OTHER PUBLICATIONS

Patel et al., "An Update on Nonmelanoma Skin Cancer", *The Journal of Clinical and Aesthetic Dermatology*, vol. 4, No. 21, pp. 20-27 (2011).

Examination Report issued Jun. 23, 2014, in corresponding Australian Patent Application No. 2014100280.

* cited by examiner

METHOD FOR TREATING SKIN LESIONS WITH INGENOL MEBUTATE

FIELD OF THE INVENTION

The invention relates to the treatment of skin lesions, including actinic keratosis, with topical application of ingenol mebutate.

BACKGROUND OF THE INVENTION

Existing topical treatments for actinic keratosis (AK) have different dosage regimens. Many treatment regimens extend over weeks or months.

The compound ingenol-3-angelate (also known as ingenol mebutate, PEP005, or (1aR,2S,5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e][10]annulen-6-yl(2Z)-2-methylbut-2-enoate; Sayed, M. D. et. al.; *Experienta*, (1980), 36, 1206-1207)) can be isolated from various *Euphorbia* species. Specifically, ingenol mebutate can be isolated from *Euphorbia peplus* (Hohmann, J. et al., *Planta Med.*, (2000), 66, 291-2940)) and *Euphorbia drummondii* by extraction followed by chromatography, e.g., as described in U.S. Pat. No. 7,449,492.

Picato® (ingenol mebutate topical gel), which is approved in many countries around the world for treatment of actinic keratosis, is available at two dosage strengths (0.015% and 0.05%) and is administered for two or three consecutive days, depending on the location of the actinic keratosis lesions; the concentration of the active compound differs depending on the location of the actinic keratosis lesions. For lesions located on the head (for example, the face or scalp), the approved dose is 0.015% ingenol mebutate applied for 3 consecutive days. For lesions located on a 'non-head' region (for example, the forearm or back), the approved dose is 0.05% ingenol mebutate applied for 2 consecutive days (see also Lebwohl et al., 2012, New England Journal of Medicine, 366: 1010-9).

The approved indications for PICATO provide that the topical gel can be applied to a contiguous area of up to 25 $cm^2$. Although pharmacokinetic studies were conducted on areas of the forearm as large as 100 $cm^2$, efficacy on areas greater than 25 $cm^2$ was not measured. However, often the AK lesions are found in larger areas of skin, so there is a need for a product to treat larger areas.

SUMMARY OF THE INVENTION

The present invention provides a topical treatment regimen for skin lesions, such as actinic keratosis (AK), which is of short duration and applicable to a large skin area, up to 250 $cm^2$ on the face, chest or balding scalp.

In a further aspect, the invention provides a composition of ingenol mebutate wherein the composition is in the form of a gel and wherein the concentration of ingenol mebutate is between about 0.015% and 0.05% by weight.

Further aspects of the present invention and further embodiments of the aspects described in the preceding paragraphs will become apparent from the following description, given by way of example and with reference to the accompanying drawings.

DETAILED DESCRIPTION OF THE INVENTION

The present inventors have now found that a suitable or optimal concentration of ingenol mebutate for treatment of skin lesions, including actinic keratosis, in a larger treatment area (i.e., an area of skin that is larger than 25 $cm^2$) is between 0.015% and 0.05%. Further, the inventors have found that concentrations of ingenol mebutate within this range are suitable for treating a larger number of pre-cancerous and cancerous lesions, wherein the lesions are present on an area of skin that is larger than 25 $cm^2$.

Accordingly, the present invention provides a method for treating or reducing the progression of cancerous or pre-cancerous lesions in a region of skin requiring treatment, the method including:
 administration of an effective amount of ingenol mebutate to the region requiring treatment;
 wherein the region requiring treatment is a contiguous area of more than 25 $cm^2$;
 wherein the effective amount of ingenol mebutate is provided as a gel formulation,
 wherein the concentration of ingenol mebutate in the gel is greater than about 0.015% and less than about 0.05%.

The invention also provides the use of ingenol mebutate in the manufacture of a medicament for the treatment or reduction of cancerous or pre-cancerous lesions in a region of skin requiring treatment, wherein the medicament is applied to a contiguous region of more than 25 $cm^2$, wherein the effective amount of ingenol mebutate is provided as a gel formulation, wherein the concentration of ingenol mebutate in the gel is greater than about 0.015% and less than about 0.05%.

In further embodiments the area to be treated is larger than 25 $cm^2$, for example, a contiguous area of at least 30, 40, 60, 80, 100, 150, 200, or 250 $cm^2$. It will also be understood that the size of the treatment area can range from at least 25 $cm^2$, to at least 500 $cm^2$ including any size which is incorporated by the above range.

It is common for pre-cancerous and cancerous skin lesions caused by sun-exposure to be found on areas of the body which are greater than 25 $cm^2$. The successful treatment of areas greater than 25 $cm^2$ have hitherto been unreported. Accordingly, in a further embodiment, the present invention provides a method for treating or reducing the progression of cancerous or pre-cancerous lesions in a region of skin requiring treatment, the method including:
 administration of an effective amount of ingenol mebutate to the region requiring treatment
 wherein the region requiring treatment is a contiguous area of more than 100 $cm^2$; and
 wherein the effective amount of ingenol mebutate is provided as a gel formulation, wherein the concentration of ingenol mebutate is greater than about 0.015% and less than about 0.05%.

In further embodiments the area to be treated is larger than 100 $cm^2$, for example, a contiguous area of at least 150, 200, or 250 $cm^2$. It will also be understood that the size of the treatment area can range from at least 25 $cm^2$, to at least 500 $cm^2$ including any size which is incorporated by the above range.

In a further embodiment, the region to be treated contains at least 5 clinically typical, visible and discrete lesions in an area larger than 25 $cm^2$. The region to be treated can have between at least 5 and 20 or more lesions, or any number of lesions within this range. For example, an individual may have 10, 11, 13 or 18 lesions in a contiguous area larger than 25 $cm^2$.

The region to be treated can be any part of the body where exposure to the sun or UV-radiation can lead to the development of cancerous or pre-cancerous lesions. In some examples, the region to be treated can be the face or scalp.

Alternatively, the lesions can be on a non-head location of the body, for example, on the trunk (chest or back) or extremities (legs and feet or arms and hands).

It will also be understood that an individual may have more than one area of skin requiring treatment. For example, an individual may have two, three, four, ten or more discrete regions, which require treatment, wherein each region can be of a size ranging from 25 cm$^2$ to more than 250 cm$^2$. The different regions requiring treatment can be on different parts of the body. For example one or more regions requiring treatment can be on the face, scalp, trunk (chest or back) or extremities.

The ingenol mebutate applied to the region to be treated is typically provided in a pharmaceutical formulation such as a gel, wherein the concentration of ingenol mebutate in the gel is between about 0.015% and 0.05%. It will be understood that the dosage of ingenol mebutate required for treatment will vary depending on the area of the body to be treated. For example, typically, lesions on the face will be treated with a lower dose than required for treatment of the extremities. For example, the concentration of ingenol mebutate can be between about 0.016% and 0.02%, between about 0.018% and 0.022%, between about 0.02% and 0.024%, between about 0.022% and 0.026%, between about 0.024% and 0.028%, between about 0.026% and 0.030%, between about 0.028 and 0.032%, between about 0.030% and 0.034%, between about 0.032% and 0.036%, between about 0.034% and 0.038%, between about 0.036% and 0.040%, between about 0.038% and 0.042%, between about 0.040% and 0.044%, between about 0.042% and 0.046%, between about 0.044% and 0.048% or between about 0.046% and 0.050%, or any concentration within the above listed ranged. In some embodiments, the concentration of ingenol mebutate if about 0.018%, 0.027%, 0.04% or about 0.05%. In a particularly preferred embodiment, the concentration of ingenol mebutate used is about 0.018%. In another embodiment, the concentration of ingenol mebutate used is about 0.027%.

Typically, the ingenol mebutate is applied to the area requiring treatment over a period of 2, 3, 4 or 5 consecutive days. In particularly preferred embodiments, the treatment period does not exceed 3 days. In some examples, the ingenol mebutate is applied to the area requiring treatment once or twice a day. In a preferred embodiment, the ingenol mebutate is applied once a day.

In a further embodiment, the area requiring treatment may not have previously received treatment, for example, cryotherapy, for treating or reducing the progression of pre-cancerous or cancerous lesions. Accordingly, in one embodiment, the treatment with ingenol mebutate represents the first-line treatment of the area requiring treatment.

The present invention also includes embodiments wherein the area requiring treatment is treated with cryotherapy after the step of administration of the effective amount of ingenol mebutate.

Previous dosage regimens for treating actinic keratoses on the chest have assumed that the same dosage regimen should be applied to both chest and forearm (with both regions falling within the definition of "trunk and extremities"). However, the findings of the present invention indicate that a significantly lower dosage of ingenol mebutate can successfully be employed for the treatment of such lesions on the chest.

Accordingly, in a further aspect, the present invention provides a method for treating or reducing the progression of cancerous or pre-cancerous lesions on a region of skin requiring treatment, the method including:

administration of an effective amount of ingenol mebutate to the region requiring treatment wherein the effective amount of ingenol mebutate is provided as a gel formulation wherein the concentration of ingenol mebutate is greater than about 0.015% and less than about 0.05%; and wherein the region requiring treatment is a contiguous area of about 250 cm$^2$ on the face, balding scalp or chest.

It further examples, the individual may have more than one area of skin requiring treatment on the face, balding scalp or chest. For example, an individual may have two, three, four, ten or more discrete regions, which require treatment, wherein each region can be about 250 cm$^2$. The different regions requiring treatment can be on different parts of the body. For example one or more regions requiring treatment can be on the face, and further regions can be on the chest or balding scalp.

In further embodiments, the region of the face, scalp and chest to be treated is a contiguous area of at least 50, 100, 150, 200, or 250 cm$^2$. In yet further embodiments, the region to be treated is full balding scalp or full face. It will be understood that the size of the treatment area can range from at least 25 cm$^2$ to at least 150 cm$^2$, or 50 cm$^2$ to 200 cm$^2$ or 100 cm$^2$ to 250 cm$^2$ or 100 cm$^2$ to 500 cm$^2$, including any size which is incorporated by the above range.

In a further embodiment, the region on the face, balding scalp or chest may contain 5 or more discrete lesions in an area of about 250 cm$^2$ or greater. The region to be treated can have between at least 5 and 20 or more lesions, or any number of lesions within this range. For example, an individual may have 10, 11, 13 or 18 lesions in a contiguous area of about 250 cm$^2$ or larger.

The outcomes of the above discussed methods of treatment are assessed by measurement of the degree of clearance of the pre-cancerous or cancerous lesions. In some embodiments, the treatment results in the complete clearance of lesions. In examples where the lesions are actinic keratoses, the outcome may be measured by observing complete clearance of actinic keratosis lesions at week 8 after commencement of treatment. Alternatively, the assessment of the treatment may be conducted by measuring a reduction in the number of lesions from baseline at week 8 after commencement of treatment.

In certain embodiments, the reduction in the number of lesions in the area requiring treatment is at least a 50% reduction. In some embodiments, the reduction is one of at least 60%, 70%, 80%, 90%, 95% or 100% reduction in the number of lesions in the area requiring treatment.

In a further aspect, the invention provides a composition of ingenol mebutate wherein the composition is in the form of a gel and wherein the concentration of ingenol mebutate is 180 μg/1 g of gel (0.018%) or 270 μg/1 g of gel (0.027%).

Conditions to be Treated

The methods and uses of the present invention may be useful for the topical treatment of dermal diseases or conditions including actinic keratosis, seborrheic keratosis, skin cancer, warts, keloids, scars, photoaged or photodamaged skin, and acne. In particular, the use of ingenol mebutate according to the present invention, is particularly useful for the topical treatment of actinic keratosis. In a further embodiment, the methods may, for instance, be useful for the topical treatment of hyperkeratotic actinic keratosis.

The uses and methods may be used for the topical treatment of skin cancers such as non-melanoma skin cancer, malignant melanoma, Merkel cell carcinoma, squamous cell carcinoma or basal cell carcinoma (including superficial basal cell carcinoma and nodular basal cell carcinoma).

The uses and methods may be used for the topical treatment of warts, e.g. human papilloma virus (HPV) infections on the skin, genitals and mouth.

The uses and methods may be used for the topical treatment of photodamaged skin such as fine lines, wrinkles and UV-ageing. UV-ageing is often manifested by an increase in the epidermal thickness or epidermal atrophy, most notably by solar elastosis, the accumulation of elastin containing material just below the dermal-epidermal junction. Collagen and elastic fibres become fragmented and disorganised. At a cosmetic level this can be observed as a reddening and/or thickening of the skin resulting in a leathery appearance, skin fragility and irregular pigmentation, loss of tone and elasticity, as well as wrinkling, dryness, sunspots and deep furrow formation.

The uses and methods may be useful for reducing or minimizing scar tissue or improving cosmesis or functional outcome in a wound. For instance, the uses and methods may be useful for improving functional outcome in a wound which is cutaneous, chronic or diabetes associated, e.g. when the wound includes cuts and lacerations, surgical incisions, punctures, graces, scratches, compression wounds, abrasions, friction wounds, chronic wounds, ulcers, thermal effect wounds, chemical wounds, wounds resulting from pathogenic infections, skin graft/transplant, immune response conditions, oral wounds, stomach or intestinal wounds, damaged cartilage or bone, amputation sides and corneal lesions.

Therefore, in some embodiments, the uses and methods are cosmetic.

Dosage Forms

The dosage forms of ingenol mebutate used in accordance with the methods and uses of the present invention are typically provided as a gel composition. The gel compositions may contain ingenol mebutate at a final concentration of about 0.005%, 0.008%, 0.012%, 0.018%, 0.027%, 0.04% or about 0.06%. A gel formulation has been described previously in WO2007/68963 and comprises ingenol mebutate, isopropyl alcohol, hydroxyethyl cellulose, benzyl alcohol, citric acid monohydrate, sodium citrate dihydrate and water. In one example, the invention provides a composition of ingenol mebutate as follows:

TABLE 1

0.018% ingenol mebutate gel formulation (1 g)

| Component | Amount | Description |
|---|---|---|
| Ingenol mebutate | 180 µg | Active ingredient |
| Isopropyl alcohol | 300 µg | Solvent |
| Hydroxyethylcellulose | 15 mg | Gelling agent |
| Benzyl alcohol | 9 mg | Solvent |
| Citric acid monohydrate | 5.6 mg | pH controlling agent |
| Sodium citrate | 1.4 mg | pH controlling agent |
| Water, purified | up to 1 g | Base |

In a further example, the invention provides the following gel formulation of ingenol mebutate:

TABLE 2

0.027% ingenol mebutate gel formulation (1 g)

| Component | Amount | Description |
|---|---|---|
| Ingenol mebutate | 270 µg | Active ingredient |
| Isopropyl alcohol | 300 µg | Solvent |
| Hydroxyethylcellulose | 15 mg | Gelling agent |
| Benzyl alcohol | 9 mg | Solvent |
| Citric acid monohydrate | 5.6 mg | pH controlling agent |
| Sodium citrate | 1.4 mg | pH controlling agent |
| Water, purified | up to 1 g | Base |

The gel compositions are typically packaged in hermetically sealed containers, e.g. a unit dose tube. In some embodiments, the unit dose tube would typically contain about 0.67 g of gel having 0.018% or 0.027% ingenol mebutate. Preferably, one unit dose tube (tube with screw cap or individual packets) may be used for one treatment area.

Due to a residual amount of medication in the tubes the actual amount applied for the patient is estimated to be 0.45 g medication per tube and two tubes are provided for each day of treatment. Thus the invention provides 0.9 g medication at 0.018% or 0.027% ingenol mebutate/250 cm2 skin per day of treatment. This amounts to an effective dose of 162 µg or 243 µg of ingenol mebutate per day.

In a number of embodiments the invention provides:

Embodiment 1

A method of treating a subject diagnosed with actinic keratosis, said method comprising applying an effective amount of ingenol mebutate to a contiguous treatment area of greater than 25 cm² located on face (e.g., the full face), balding scalp (e.g., the full balding scalp) or chest for two or three days.

Embodiment 2

The method of Embodiment 1, wherein the method provides reduction in the number of actinic keratosis lesions in the treated area. In certain embodiments, the reduction in the number of actinic keratosis lesions in the treated area is at least 50% after treatment, or at least 60%, 70%, 80%, 90%, 95%, or 100% reduction in the number of actinic keratosis lesions in the treated area.

Embodiment 3

The method of Embodiment 1, wherein the two or three treatment days are all consecutive days.

Embodiment 4

The method of any of the Embodiments 1-3, wherein the treated area is up to approximately 250 cm². In certain embodiments, the contiguous treatment area is up to 50 cm², 100 cm², 150 cm², 200 cm² or 250 cm². In certain embodiments, the contiguous treatment area is greater than 25 cm², 50 cm², 100 cm², 150 cm², or 200 cm².

Embodiment 5

The method of any of the Embodiments 1-4, wherein the ingenol mebutate is applied in a topical formulation comprising between about 0.018% and about 0.027% ingenol mebutate by weight. In certain embodiments, the topical formulation comprises about 0.018%, 0.020%, 0.022%, 0.024%, 0.026% or 0.027% ingenol mebutate by weight.

Embodiment 6

The method of Embodiment 1, wherein the amount of ingenol mebutate applied is 0.9 g medication at a concentration of 0.018% or 0.027%/per day/250 cm$^2$ treated area.

Embodiment 7

The method of any of the Embodiments 1-6, wherein the ingenol mebutate is formulated in a gel. In certain embodiments, the gel further comprises isopropyl alcohol. In certain embodiments, the gel further comprises benzyl alcohol. In certain embodiments, the gel further comprises a pH modifier. In certain embodiments, the gel has a pH in the range of about 3.0-4.0.

Embodiment 8

The method of any of the Embodiments 1-7 above, wherein the treatment is for 2 consecutive days.

Embodiment 9

The method of any of the Embodiments 1-7 above, wherein the treatment is for 3 consecutive days.

In certain embodiments, the contiguous treatment area of greater than 25 cm$^2$ is located on the face (e.g., the full face) of the subject. In other embodiments, the contiguous treatment area of greater than 25 cm$^2$ is located on the balding scalp (e.g., the full balding scalp) of the subject. In other embodiments, the contiguous treatment area of greater than 25 cm$^2$ is located on the chest of the subject.

In certain embodiments, the ingenol mebutate is applied by applying a pharmaceutical formulation comprising ingenol mebutate.

In certain embodiments, the ingenol mebutate is applied once per day. In certain embodiments, the ingenol mebutate is applied twice per day.

In certain embodiments, the amount of ingenol mebutate applied per day is between about 150 micrograms and about 250 micrograms, more preferably about 162 micrograms or about 243 micrograms per day.

In certain embodiments of the above methods, the subject has not been treated with cryotherapy in the contiguous treatment area of greater than 25 cm$^2$ prior to the step of applying an effective amount of ingenol mebutate to the contiguous treatment area.

In another aspect, the invention provides a method of treating a subject diagnosed with actinic keratosis, said method comprising applying an effective amount of a topical formulation comprising between about 0.018% and about 0.027% ingenol mebutate by weight to a contiguous treatment area of greater than 25 cm$^2$ located on face, balding scalp or chest once or twice daily for two or three days consecutive days.

In another embodiment, the invention provides a method of treating a subject diagnosed with at least one cancerous or pre-cancerous lesion on a region of skin, said method comprising applying an effective amount of ingenol mebutate to a contiguous treatment area of greater than 25 cm$^2$ located on face, chest or balding scalp for 2 or 3 days, wherein the effective amount of ingenol mebutate is applied in a topical formulation comprising greater than about 0.015% and less than about 0.05% ingenol mebutate by weight.

In certain embodiments, the at least one lesion is selected from the group consisting of: actinic keratosis, nevoid basal cell carcinoma and superficial basal cell carcinoma, seborrheic keratosis, skin cancer, warts, keloids, scars, photoaged or photodamaged skin, and acne.

In certain embodiments, the two or three treatment days are consecutive days.

In certain embodiments, the treatment area is up to approximately 250 cm$^2$ in area.

In certain embodiments, the effective amount of ingenol mebutate is applied in a topical formulation comprising between about 0.018% and about 0.027% ingenol mebutate by weight.

In certain embodiments, the amount of ingenol mebutate applied is approximately 0.9 g medication at a concentration of 0.018% or 0.027%/per day/250 cm$^2$ treated area.

In certain embodiments, the ingenol mebutate is formulated in a gel.

In certain embodiments, the subject has not been treated with cryotherapy in the contiguous treatment area.

In certain embodiments, the at least one lesion is actinic keratosis and the treatment provides reduction in the number of actinic keratoses in the treated area.

In certain embodiments, the region requiring treatment is a contiguous area on the face, balding scalp or chest of up to about 250 cm$^2$.

In another aspect, the invention provides a method of treating a subject diagnosed with actinic keratosis, said method comprising applying an effective amount of a topical formulation comprising between about 0.018% and about 0.027% ingenol mebutate by weight to a contiguous treatment area of greater than 25 cm$^2$ located on face, balding scalp or chest once or twice daily for two or three days consecutive days.

In another aspect, the invention provides a pharmaceutical formulation of ingenol mebutate, wherein the composition is in the form of a gel and wherein the concentration of ingenol mebutate in the gel is between about 0.015% and about 0.05% by weight.

In certain embodiments, the concentration of ingenol mebutate in the gel is between about 0.018% and about 0.027% by weight.

Example 1

Treatment of skin areas up to 250 cm$^2$ on face, balding scalp and chest with ingenol mebutate (ingenol-3-angelate) is studied. Based on data from a limited number of AK subjects treated with ingenol mebutate on areas of the forearm up to 100 cm$^2$, it is anticipated that lower exposure of ingenol mebutate will be needed with larger treatment areas. On average, the subjects treated with ingenol mebutate gel 0.05% on 100 cm$^2$ had maximum composite local skin reaction (LSR) scores approximately 3 points higher than subjects treated on 25 cm$^2$ based on post hoc analysis of data. Whereas the clinical development program for ingenol mebutate gel showed that the optimal treatment regimen for face entailed once daily dosing for 3 days, it is possible that a shorter duration of just 2 days might be feasible for larger areas. Lower exposure could alternatively be obtained by decreasing the dose while maintaining the number of treatment days. The present invention provides optimized dosage regimens for larger areas on face, balding scalp and chest. The present invention provides a topical treatment regimen for actinic keratosis (AK) which is of short duration and applicable to a large skin area, up to 250 cm² on face, balding scalp or chest.

The treatment regimen provided by the present invention is supported by two clinical studies: Part 1—dose escalation; and Part 2—efficacy.

Part 1 is designed with treatment of AK's on face only. The starting dose and regimen will be 0.005% daily for 3 days. Part 1 will identify maximum tolerated dose for once daily application for 3 consecutive days regiment. Then subjects will be recruited to the once daily application for 2 consecutive days regimen and dose escalating until the maximum tolerated dose has been reached also for this schedule.

Maximum tolerated dose (MTD) will be defined as the highest dose at which less than 4 subjects out of 12 experience on dose limiting toxicity (DLT). Dose limiting toxicity is pre-defined grades of LSRs.

Local skin reactions (LSRs) sometimes occur in the treated area. Often LSRs are quantified by a scale evaluating the following types of skin reactions: erythema, flaking/scaling, crusting, swelling, vasiculation/postulation, and erosion/ulceration which are categorized into categories 0-4 depending on the severity of the reactions.

DLT was defined as one or more of the following three LSRs:

Crusting Grade 54, erosion/ulceration Grade 4, vesiculation/postulation Grade 4 or two or more of the following five LSRs: Erythema Grade 4, crusting Grade 3, Swelling Grade 4, Erosion/Ulceration Grade 3, Vesiculation/postulation Grade 3.

In part 2 of the trial, the efficacy of the MTD and the dose level below the MTD will be tested in four treatment groups with 62 subjects in each (3 day vs 2 day application on face, chest or scalp). Two vehicle arms will be included for 2 day and 3 days application.

Part 2 of the trial is evaluated with regard to efficacy in the different doses after once daily treatment for 2 or 3 consecutive days compared to vehicle gel.

Also the safety of ingenol mebutate gel in different doses after once daily treatment for 2 or 3 consecutive days compared to vehicle gel is evaluated.

The outcome of the treatment is measured as either
(a) complete clearance of AKs at week 8 or
(b) reduction in AK count from baseline at week 8.

Also the treatment provides the following safety measures:
(a) adverse events and serious adverse events, and
(b) LSRs.

Subjects who qualify for the trial must have 5 to 20 clinically typical, visible and discrete actinic keratosis on the face (part 1), or face, balding scalp or within a contiguous area of approximately 250 cm² on the chest (part 2).

In part 1a the objective was to find the MTD for ingenol mebutate gel after once daily treatment for 3 consecutive days. Whereas the trial was designed for the possibility of up to seven different doses of ingenol mebutate gel could be invested in cohorts of 3 to 12 subjects, the actual trial only investigated 6 doses. The number of subjects in each cohort depended on the number of observed DLTs. However, the MTD was always confirmed in a cohort of 12 subjects. The doses were administered in an escalating manner following review of safety and tolerability data performed by the dose escalation committee. For part 1a, evaluation of the safety and tolerability data was performed after visit 6/day 8.

In part 1b the objective was to find the MTD for ingenol mebutate gel after once daily treatment for 2 consecutive days. The starting dose for part 1b was the dose level above the MTD found in part 1a. In this particular trial it was 0.04% and 0.06%. The doses were administered in an escalating manner following review of safety and tolerability data performed by the dose escalation committee. This was evaluated after visit 5, day 8.

Part 2 is a multicenter, randomised, double-blind, parallel group and vehicle-controlled trial. In part 2, the objective is to evaluate efficacy of ingenol mebutate gel in two different doses, after once daily treatment for 2 or 3 consecutive days, respectively, compared to vehicle gel. The dose levels to be investigated correspond to the MTD levels identified in part 1a and part 1b and the dose levels just below the identified MTD levels. In the present trial, it is 0.027% and 0.018%. In part 2 the treatment area can be full face, full balding scalp or a contiguous area of approximately 250 cm² on the chest.

Subjects are allocated to ingenol mebutate gel or vehicle gel in a randomised manner (4 active treatment arms with 62 subjects each and 2 vehicle arms with 31 subjects each).

Randomisation is stratified by located (face/chest or scalp) of the treatment area. The enrollment is controlled so that approximately 20% of the subjects are treated on the scalp and approximately 80% of the subjects are treated on the face or chest.

The subjects are followed for 8 weeks after first application. Complete clearance is assessed at week 8.

Exclusion criteria are: incompletely healed wound, basal cell carcinoma or squamous cell carcinoma within 5 cm of treatment area, or prior treatment with ingenol mebutate gel on the treatment area, or atypical clinical appearance on the lesions such as hypertrophic, hyperkeratotic or cutaneous horns, and/or recalcitrant disease such as non-responding to cryotherapy on two previous occasions.

The patients are scheduled for 7 visits:
Visit 1: within 35 days prior to day 1
Visit 2: day 1 application of trial medication
Visit 3: application of trial medication/LSR assessment
Visit 4: application of trial medication (only part 1a)/LSR assessment
Visit 5: day 4 in part 1a and day 8±1 day in part 1 b. LSR assessment.

LSRs are evaluated at all visits following the first application of trial medication. All trial medication is applied during a patient visit in part 1.

Efficacy analyses will be based on the full analysis set, which will be defined as all randomised subjects. Per protocol analysis set will be used as an efficacy subset and will be defined as subjects in the full analysis set who complete the study without major protocol deviations. Analysis based on the full analysis set will be considered the primary analysis, whereas the per protocol analysis serves a supportive purpose. Safety analyses will be based on the safety analysis set, which is defined as all subjects who receive at least one application of trial medication and have safety information available post treatment.

Randomisation will be stratified by anatomical location (face/chest or scalp) in order to obtain at least subjects per site per treatment arm, trial sites yielding fewer than 20 subjects will be combined together into "analysis sites" in order of geographical proximity. The exact composition of these analysis sites will be determined and documented prior to breaking the trial blind.

Complete clearance of AKs at week 8 will be analysed by log binomial regression with factors: treatment group, anatomical location (face/chest or scalp) and analysis site. The number of baseline lesions will be included as a continuous variable. The rate ratios of each active group and the corresponding vehicle group will be presented together with their 95% confidence intervals.

To account for multiple testing, the four tests will be performed using a closed test procedure. The pre-defined hierarchical order of testing is determined as follows: the highest dose within the 2 day treatment regimen will be tested first and provided a significant result is observed, the lowest dose within the 2 day treatment regimen will be tested, then the highest dose within the 3 day treatment regimen will be tested and finally the lowest dose within the 3 day treatment regimen will be tested thus securing that the overall significance level does not exceed 5%.

As a supportive analysis, a Cochran-Mantel-Haenszel test adjusting for analysis site will be performed. A last observation carried forward approach will be used to account for missing values. A sensitivity analysis will be conducted, where subjects with no week 8 AK count are considered as not having complete clearance, if they have received active treatment and are considered as having complete clearance, if they have received vehicle. To account for multiple testing among the secondary endpoints, a hierarchical order of testing is determined as follows: first the four comparisons in terms of reduction in AK count from baseline to week 8 are tested using the same order as described for the primary endpoint. Provided the tests are significant, the procedure is repeated for the second endpoint, partial clearance.

Reduction in AK count from baseline to week 8 will be tabulated (mean, 95% confidence interval, median, min, max) by treatment group and analysed by negative binomial regression on the number of lesions at week 8 including the log baseline AK count as offset and with factors: treatment group, anatomical location (face/chest, scalp) and analysis site. The rate ratios of each active group and the corresponding vehicle group will be presented together with their 95% confidence intervals.

Partial clearance of AKs at Week 8, defined as at least 75% reduction from baseline in number of AKs will be analysed in the same way as the primary endpoint.

Subgroup Analyses by Anatomical Location:

The number of subjects with complete clearance and partial clearance as well as a summary of the reduction in AK count from baseline to week 8 will be tabulated by anatomical location (face/chest/scalp). No formal hypotheses will be tested in these subgroup analyses.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Those skilled in the art will recognize, or be able to ascertain using no more than routine experimentation, many equivalents of the specific embodiments of the invention described herein. Such equivalents are intended with be encompassed by the following claims.

The invention claimed is:

1. A method of treating a subject diagnosed with at least one cancerous or precancerous lesion on a region of skin, said method comprising applying an effective amount of ingenol mebutate to a contiguous treatment area of greater than 25 $cm^2$ located on face, chest or balding scalp for 2 or 3 days, wherein the effective amount of ingenol mebutate is applied in a topical formulation comprising between about 0.018% and about 0.027% ingenol mebutate by weight.

2. The method of claim 1, wherein the at least one lesion is selected from the group consisting of: actinic keratosis, nevoid basal cell carcinoma and superficial basal cell carcinoma, seborrheic keratosis, skin cancer, warts, keloids, scars, photoaged or photodamaged skin, and acne.

3. The method of claim 1, wherein the two or three treatment days are consecutive days.

4. The method of claim 1, wherein the treatment area is up to approximately 250 $cm^2$ in area.

5. The method of claim 1, wherein the amount of ingenol mebutate applied is approximately 0.9 g medication at a concentration of 0.018% or 0.027%/per day/250 $cm^2$ treated area.

6. The method of claim 1, wherein the ingenol mebutate is formulated in a gel.

7. The method of claim 1, wherein the subject has not been treated with cryotherapy in the contiguous treatment area.

8. The method of claim 1, wherein the at least one lesion is actinic keratosis and the treatment provides reduction in the number of actinic keratoses in the treated area.

9. The method of claim 1, wherein the region requiring treatment is a contiguous area on the face, balding scalp or chest of up to about 250 $cm^2$.

10. A method of treating a subject diagnosed with actinic keratosis, said method comprising applying an effective amount of a topical formulation comprising between about 0.018% and about 0.027% ingenol mebutate by weight to a contiguous treatment area of greater than 25 $cm^2$ located on face, balding scalp or chest once or twice daily for two or three days consecutive days.

11. A pharmaceutical formulation of ingenol mebutate, wherein the composition is in the form of a gel and wherein the concentration of ingenol mebutate in the gel is between about 0.018% and about 0.027% by weight.

* * * * *